(12) United States Patent
Barnea

(10) Patent No.: US 6,270,458 B1
(45) Date of Patent: Aug. 7, 2001

(54) CERVIX DILATION AND LABOR PROGRESSION MONITOR

(75) Inventor: Ofer Barnea, Tel Aviv (IL)

(73) Assignee: Barnev Inc., Tel Aviv (IL)

( * ) Notice: Subject to any disclaimer, the term of this patent is extended or adjusted under 35 U.S.C. 154(b) by 0 days.

(21) Appl. No.: 09/263,096

(22) Filed: Mar. 5, 1999

(51) Int. Cl.$^7$ .............................. A61B 8/00; A61B 5/103
(52) U.S. Cl. ......................... 600/438; 600/588; 600/591
(58) Field of Search .................................. 600/437, 438, 600/449, 459, 587, 588, 591

(56) References Cited

U.S. PATENT DOCUMENTS

| | | | |
|---|---|---|---|
| 5,222,485 | * | 6/1993 | Jerath .................................. 600/437 |
| 5,438,996 | * | 8/1995 | Kemper et al. ...................... 600/449 |
| 5,515,853 | * | 5/1996 | Smith et al. ...................... 128/916 X |
| 5,713,371 | * | 2/1998 | Sherman et al. .................... 600/449 |
| 5,935,061 | * | 8/1999 | Acher et al. ........................ 600/304 |

\* cited by examiner

*Primary Examiner*—Francis J. Jaworski
(74) *Attorney, Agent, or Firm*—Mark M. Friedman

(57) ABSTRACT

A device and method for monitoring cervical dilation, and descent of the presenting part, during labor. An extracorporeally located ultrasound transmitter transmits ultrasound signals into the body of the patient. Small ultrasound reflectors located on either side of the cervical os, and on the fetal presenting part, reflect the ultrasound signals back to extracorporeal ultrasound receivers. Spectral and acoustic characteristics of the received ultrasound signals are analyzed to identify the relative locations of the reflectors, and the trigonometric relationships between the reflectors and transmitters are used to calculate the degree of cervical dilation, and the descent of the fetal presenting part. In an alternative embodiment, passive ultrasound receivers are used instead of ultrasound reflectors.

15 Claims, 7 Drawing Sheets

CERVIX DILATION AND LABOR PROGRESSION MONITOR

FIELD AND BACKGROUND OF THE INVENTION

The present invention relates to the field of medical monitoring instrumentation in general, and in particular, to the field of labor monitoring devices.

It is well known that the process of labor and childbirth entails the gradual thinning and dilation of the uterine cervix, in response to coordinated uterine contractions, resulting in the eventual expulsion of the fetus through the fully dilated uterine cervix and birth canal. As such, the degree, and rate of progression, of cervical dilation is closely monitored by hospital staff during labor and childbirth, and is considered to be the cardinal indicator of the progression of labor. Slow or inadequate cervical dilation may indicate inefficient or pathological labor, and is often an indication for medical or surgical intervention, particularly if accompanied by evidence of fetal distress. In addition, the gradual descent of the fetal head through the birth canal, also referred to as the descent of the "presenting part", is repeatedly assessed during labor, and serves as an additional descriptor of the progress of childbirth.

Cervical dilation does not ordinarily proceed at a constant rate. Typically, dilation is slow until 4–5 cm dilation is reached, more rapid until dilation is nearly complete, and then slower again until full dilation of 10 centimeters is achieved. Thereafter, the second stage of labor, during which the fetus passes through the dilated cervix and birth canal, begins.

Due to their cardinal importance as indicators of the progress of labor, the amount of cervical dilation and the descent of the presenting part are regularly determined by professional attendants (such as midwives and obstetricians) during the course of labor, usually by means of a manual vaginal examination. On average, ten manual vaginal examinations are required per labor. Manual vaginal examinations, however, suffer from several disadvantages: they are embarrassing and uncomfortable for the patient, subjective, inaccurate, provide very intermittent information, can introduce infection into the uterus, require manual charting, and add to the medical staff workload.

Although several monitoring devices are routinely used during the course of labor (such as fetal heart rate monitors, fetal oxygen saturation monitors [pulse oxymetry], uterine activity monitors [tocometry], and maternal vital signs monitors), automatic monitoring of cervical dilation and descent of the presenting part is not yet available. This is despite the fact that several methods for measuring cervical dilation have been described. These methods include:

1) Obstetric gloves incorporating a measuring string or measuring tape.
2) Finger mounted angular V calipers.
    This device is attached to the obstetricians fingers, and is inserted into the vagina whenever a measurement is required. The obstetrician measures dilation by spreading his fingers in the sane way as done in regular manual vaginal examination. A mechanical scale, potentiometer, or strain gauge measures the angle between the caliper alms, and the measurement is converted to a dilation value. Both of the above devices suffer from the deficiencies described above for standard manual vaginal examinations.
3) Cervix mounted angular V calipers.
    This device is placed in the vagina and attached to two points on opposite sides of the cervix to each other. A mechanical scale, potentiometer, or strain gauge then measures the angle between the caliper arms, and the measurement is converted to a dilation value. This device suffers from the deficiency that it substantially occupies the vagina, thus interfering with other monitoring and treatment activities. It therefore has to be removed and reinserted repeatedly. In addition, it is uncomfortable to the patient, may require manual charting, and is difficult to install, thus adding to the medical staff workload.
4) Induction transmitters and receivers clamped to two sides of the cervix opposite to each other.
    As the distance between the primary and secondary induction windings affects the induced signal, the distance between them (which is equal to the cervical diameter) can be measured. This device suffers from the deficiency that it functions effectively only until about 5–7 cm dilation, whereas manual measurements are required until 10 cm dilation. In addition, the insertion of other instruments into the vagina and the cervix, as is often done during labor, adversely effects the measurement readings of the device, rendering it impractical for clinical use.
5) A multi-switch membrane that is inserted into the uterus, and pressed between the cervical internal os and the fetal head.
    As the switches in the cervical opening are not pressed, while those within the uterus are, an ongoing indication of the progress of dilation is rendered. This device suffers from several deficiencies. Firstly, it is necessary to insert the membrane between the fetus and the uterine wall, which is technically difficult, particularly before the amniotic sack has ruptured, and undesirable afterwards due to the risk of introducing infection. Secondly, the membrane often shifts, giving rise to false measurements. In addition, as the membrane crosses the cervix from one side to the other after placement, the entrance to the uterus is obstructed, thus interfering with other monitoring and treatment activities. Other disadvantages are that the device is uncomfortable for the patient, and adds to the medical staff workload.

None of the devices described above are able to monitor descent of the presenting part.

It is well known that it is possible to accurately and continuously measure the degree of dilation of a hollow organ by means of ultrasound tissue imaging. Successfully measuring cervical dilation by this technique would obviate the deficiencies and drawbacks inherent to the alternative techniques described above. As such, there has been much interest in developing ultrasound-based cervical dilation monitors. All such devices described to date incorporate two transducers, one being an ultrasound transmitter and the other an ultrasound receiver, which are attached to the cervix. The time taken for ultrasound waves transmitted from the transmitter to reach the receiver is translated into the distance between the two transducers, which represents the diameter of the cervix. Devices of this nature have been shown to operate satisfactorily under well-controlled laboratory conditions. However, in-vivo, the presence of air and differing biological tissues within the vagina creates an inhomogeneous medium between the two transducers. This lowers the signal-to-noise ratio and results in inaccurate ultrasound measurements and low repeatability. Furthermore, the probe inserted into the vagina, being a complete ultrasound transmitter, is relatively large (and thus must be removed to allow other monitoring and treatment activities), and may be uncomfortable for the patient. In addition, as mentioned above regarding non-ultrasound based labor monitors, devices of this nature do not monitor descent of the presenting part.

There is therefore a need for an ultrasound-based cervical dilation monitor which is capable of accurately and automatically monitoring the progress of cervical dilation and decent of the presenting part, without the need to introduce a large ultrasound probe into the vagina.

SUMMARY OF THE INVENTION

The present invention is an ultrasound device for monitoring cervical dilation, and descent of the presenting part, during childbirth. The monitor consists of three major components: a) a plurality of ultrasound transducers, located externally on the abdomen of the patient being monitored, b) multiple small, disposable plastic units, being either acoustic signal reflectors or passive ultrasonic receivers, which are attached internally around the circumference of the cervix, or to the presenting part of the fetus, and c) a microprocessor-based data processing and display unit, located externally to the patient and attached to the ultrasound transducers and receivers by means of cable.

The extracorporeal ultrasound transducers transmit ultrasonic acoustic signals into the body of the mother. By extracorporeal is meant that the transducers are located on the outside of the body of the patient, as opposed to within a body cavity. In a first embodiment, the ultrasonic signals are received by miniature acoustic signal reflectors that are attached to the cervix or the fetal presenting part, and reflected back to the extracorporeal transducers. These acoustic signal reflectors include inorganic materials such as steel, and are referred to hereinafter as "inorganic ultrasound reflectors" so as to differentiate them from organic ultrasound reflectors, such as the patients tissues and organs, which are encountered by the transmitted ultrasonic acoustic signals. In a second embodiment the ultrasonic signals are received by miniature ultrasonic receivers that are attached to the cervix or the fetal presenting part. Hereinafter, the term "internal surface" is used to refer to the cervix, the fetal presenting part, or any other surface located within a body cavity (such as the vagina) of a patient and upon which medical devices such as acoustic reflectors or receivers can be placed. The extracorporeal transducers and ultrasonic receivers input directly to the data processing and display unit, which analyzes the time or phase characteristics of the received waves with each other. Two methods of ultrasound transmission and analysis can be utilized. Thus in one embodiment short acoustic pulses are transmitted, and the measured time delay between signal transmission and reception is analyzed. This time delay is hereinafter referred to as the "ultrasound time of flight". In a second embodiment, continuous or long acoustic signals are transmitted, and the phase difference between transmitted and received signals is analyzed. This phase difference is hereinafter referred to as the "ultrasound phase shift". By utilizing geometric or trigonometric techniques, or by analyzing spectral characteristics of the received signals, the locations of the acoustic reflectors or ultrasonic receivers relative to each other can be calculated, thus providing a description of the degree of cervical dilation and descent of the presenting part. A special applicator is used to place the reflectors or receivers on the cervix in a safe and sterile manner. The attachment of a reflector or receiver to the fetal presenting part is achieved in a similar manner to the attachment of a fetal scalp ECG electrode.

Since the ultrasound transducers are located extracorporeally, while the reflectors or ultrasound receivers are on the cervix, the acoustic signals traverse only the intervening biological tissue, but not the air-filled vaginal lumen. The signal-to-noise ratio is thus high, resulting in high quality ultrasound localization of the reflectors or receivers. Furthermore, as the active ultrasound transmitting component of the device is external, and only the reflectors or passive receivers are located internally, the components which are attached to the cervix are small. The device is thus comfortable for the patient, and does not preclude the introduction of other medical devices into the vagina. As the internally located components are passive, and do not actively transmit acoustic energy, the potential risk to the fetus from excessive ultrasound exposure is lessened. In addition, the transmission of acoustic waves from an external source, as opposed to a transmitter located on the cervix, allows for the power of the transmitted waves to be increased, and for the use of sophisticated transducer arrays.

According to the teachings of the present invention there is provided, a device for monitoring the progress of labor in a subject, including at least one extracorporeal ultrasound transmitter, operative to transmit ultrasound signals into the subject; at least one inorganic ultrasound reflector, operative to reflect the transmitted ultrasound signals, the reflector being placeable on an internal body surface within the subject; at least one extracorporeal ultrasound receiver, operative to receive the reflected ultrasound signals, and a processor, operative to calculate a location of the reflector from the received reflected ultrasound signals, the location being a descriptor of the progress of labor in the subject. There is further provided a device for monitoring the progress of labor in a subject, including at least one extracorporeal ultrasound transmitter, operative to transmit ultrasound signals into the subject; at least one ultrasound receiver, operative to receive the transmitted ultrasound signals, the at least one receiver being placeable on an internal body surface within the subject, and a processor, operative to calculate at least one location of the at least one ultrasound receiver from the received ultrasound signals, the at least one location being a descriptor of the progress of labor in the subject. There is further provided a method for monitoring the progress of labor in a subject, including transmitting ultrasound signals from an extracorporeal location; reflecting the transmitted ultrasound signals off at least one inorganic reflector at an internal body surface of the subject; receiving the reflected signals at an extracorporeal location, and calculating a descriptor of the progress of labor from the received reflected signals. There is further provided a method for monitoring the progress of labor in a subject, including transmitting ultrasound signals from an extracorporeal location; receiving the transmitted signals at a plurality of locations on an internal body surface of the subject, and calculating a descriptor of the progress of labor from the received signals.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a cervical dilation and labor progress monitor.

The principles and operation of a cervical dilation and labor progress monitor, according to the present invention, may be better understood with reference to the drawings and the accompanying description.

Figure 1:
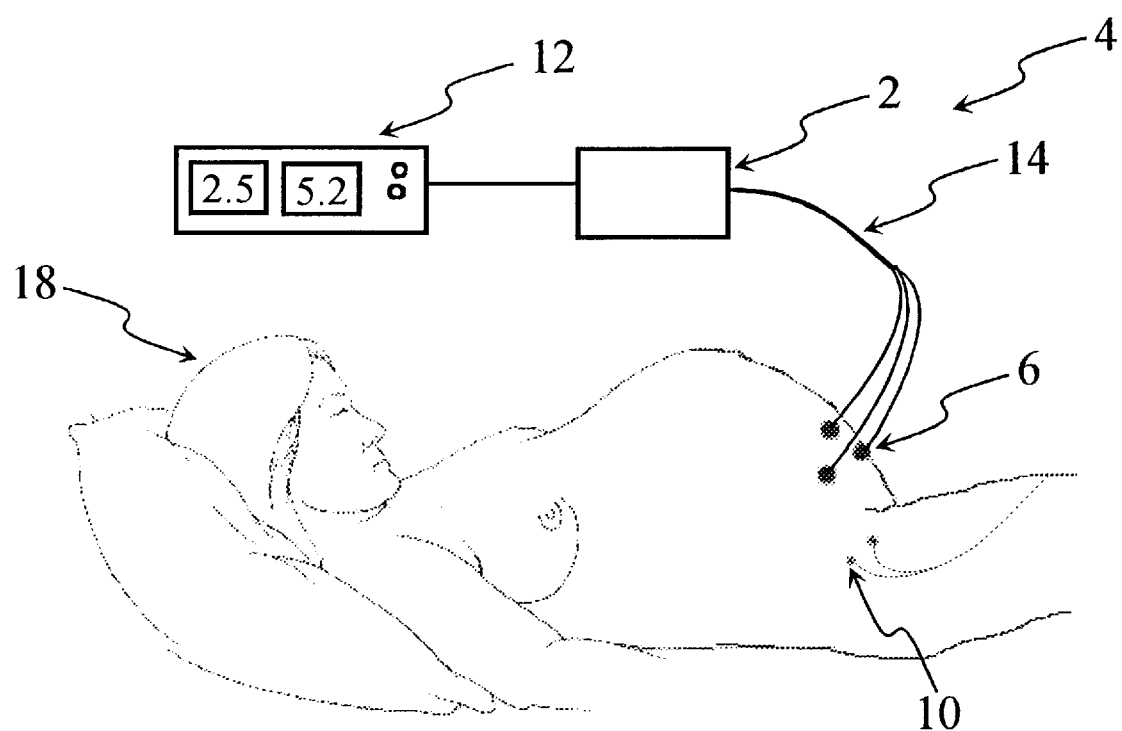
FIG. 1 is a line drawing of the physical components of a cervical dilation and labor progress monitor.

Turning now to the figures, FIG. 1 is a line drawing of the physical components of a preferred embodiment of the device of the current invention. As can be seen, the device 4 includes a data processing unit (DPU) 2. DPU 2 contains a microprocessor which controls the functioning of all electronic components of device 4 and performs all data manipulations and calculations. An 80486 processor (Intel, U.S.A.) is suitable for use as the microprocessor of DPU 2. DPU 2 receives data input from ultrasound transducers 6 and from a standard user interface, such as a keyboard or a touch-screen (not shown). Ultrasound transducers 6 may be either signal transmitters, signal receivers, or both, and are standard piezoelectric or magnetorestrictive transducers of the type routinely used in medical ultrasound applications. Examples of ultrasound transducers suitable for use as ultrasound transducers 6 are ultrasonic contact transducers manufactured by Panametrics Inc. (Weltham, Mass.), having frequencies of 50 kHz, 100 kHz, 500 kHz, or 1 mHz; a beam angle of at least twenty degrees; a transducer head diameter of less than 2 cm; and an operating temperature of between zero and fifty degrees centigrade. Ultrasound transducers 6 are positioned on the abdomen of a patient 18, and held in place by straps (not shown). One or more of ultrasound transducers 6 functions as a signal transmitter and transmits acoustic ultrasound signals into the abdomen of a patient 18.

In this embodiment, at least two ultrasound reflectors 10 are located on the circumference of the celvix of patient 18. Ultrasound reflectors 10 are positioned on the cervix of patient 18 using a specialized applicator (not shown). The applicator utilizes a speculum-like component to open the vagina and reveal the cervix, and a probe-like component to introduce ultrasound reflectors 10 and affix them to the cervix in a sterile manner. Ultrasound reflectors 10 are affixed to the cervical tissue by means of hooks or clamps. Ultrasound reflectors 10 are made of a material in which the speed of sound is greater than the speed of sound in air or biological tissue, so as to facilitate differentiation between echoes reflected from a tissue-reflector interface and echoes reflected from a tissue-air interface. Ultrasound reflectors 10 are thus small (approximately 5 mm in diameter) curved disks constructed of silicone, and containing an air bubble, or an element (such as steel) which has an acoustic impedance that is significantly different from that of biological tissue, in their center.

The curvature of ultrasound reflectors 10 serves to reflect acoustic waves in a wide angle beam, such that multiple ultrasound receivers (i.e. ultrasound transducers 6) located on the abdomen of patient 18 may receive the reflected signals. The ultrasound signals transmitted by one or more of ultrasound transducers 6 are thus reflected by ultrasound reflectors 10, and the returning echoes are received by all of ultrasound transducers 6, functioning as active signal receivers. The acoustic signals received by ultrasound transducers 6 are then input to DPU 2 via a connecting cable 14. DPU 2 then analyzes the acoustic signals, as described in detail below, and calculates the relative spatial relationships between each of ultrasound reflectors 10. As ultrasound reflectors 10 are located on the circumference of the cervix of patient 18, DPU 2 is able to calculate the degree of instantaneous cervical dilation. This data is then depicted on a display 12. Display 12 may be a CRT or an LCD screen, on which both dilation and rate of dilation are depicted in numerical and graphic formats. DPU 2 can be programmed to activate an audio or visual alarm when dilation or rate of dilation varies from predefined standard values stored within DPU 2.

Figure 2:
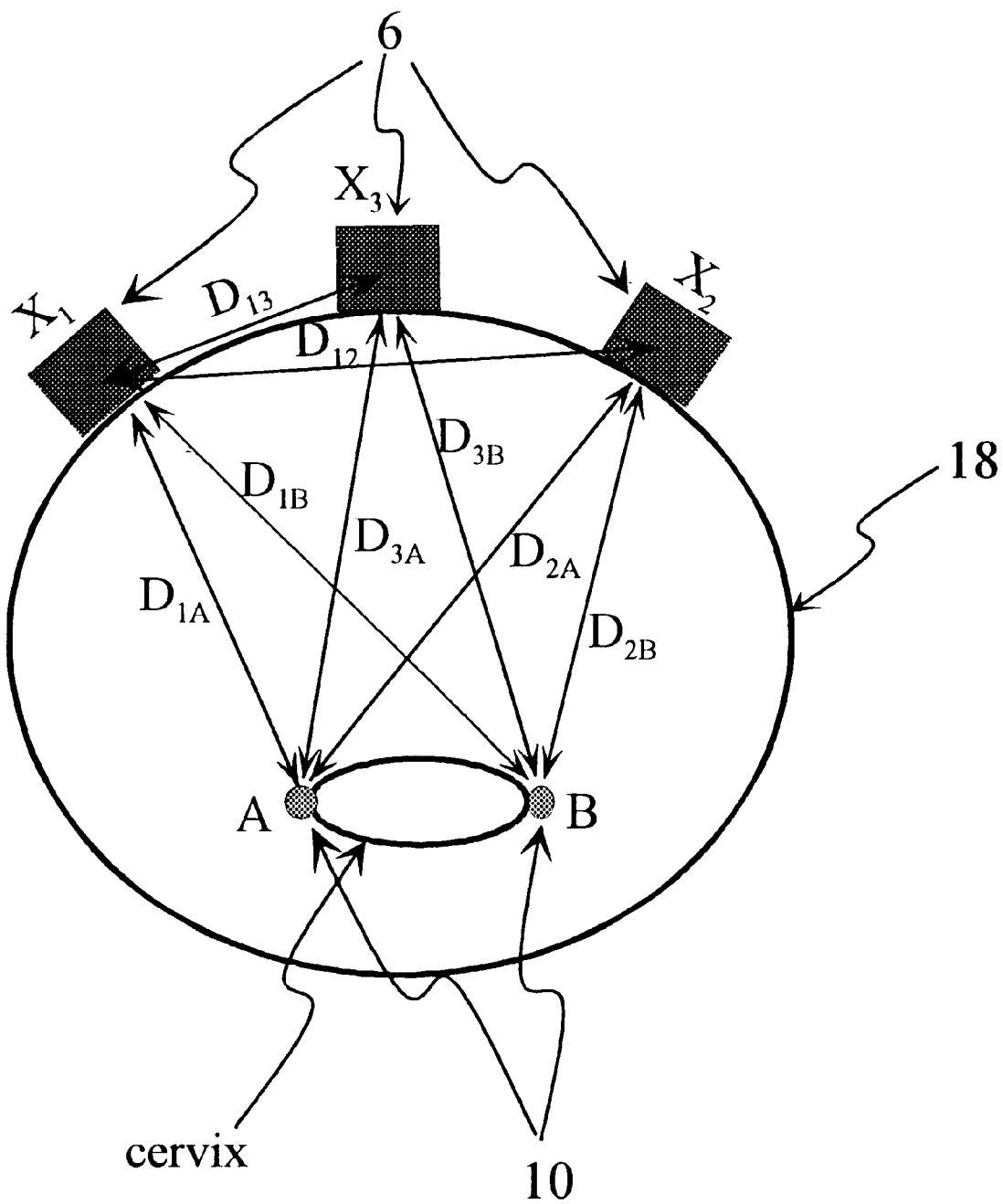
FIG. 2 is a schematic depiction of the distances and spatial relationships between extracorporeal ultrasound transducers and cervical ultrasound reflectors according to a first preferred embodiment of the current invention.

FIG. 2 illustrates the principles underlying a first preferred embodiment of the current invention. In this embodiment, three ultrasound transducers ($X_1$, $X_2$, and $X_3$) are placed on the abdomen of patient 18, and correspond to ultrasound transducers 6 of FIG. 1. The distances between each of transducers $X_1$, $X_2$, and $X_3$, and their spatial relationship to each other, are known and are entered into tile processor of DPU 2. Transducer $X_1$ comprises an ultrasound transmitter and receiver, while transducers $X_2$ and $X_3$ are acoustic receivers only. Transducers $X_1$, $X_2$, and $X_3$ are not oriented in a straight line relative to one another, but are arranged in a triangular format. Ultrasound reflectors 10, which are attached to the circumference of the external os of cervix 20 at essentially opposite ends to each other, comprise two acoustic reflectors (A and B) with somewhat different internal structures to each other, such that the reflections they create each have different acoustic spectra from the original transmitted signal, and from each other. This makes each reflector identifiable by the characteristic acoustic spectrum of its echo. Transducer $X_1$ transmits ultrasound signals towards cervix 20. The transmitted signals are reflected by reflectors A and B, and the reflected echoes are received by transducers $X_1$, $X_2$, and $X_3$. DPU 2 then utilizes standard signal processing techniques, such as Fourier transforms, filters and wavelet transform analysis, to identify each reflector in terms of its characteristic acoustic spectrum. Once each received signal has been identified as originating from either reflector A or reflector B, the received signals are analyzed trigonometrically in conjunction with the signals transmitted by transducer $X_1$, so as to calculate the relative distance between reflectors A and B. In accordance with this embodiment of the current invention, transducer $X_1$ may transmit short acoustic pulses, in which case the measured time delay between transmitted and received pulses is analyzed by DPU 2, or transducer $X_1$ may transmit long acoustic signals, in which case the phase difference between transmitted and received signals is analyzed by DPU 2. As reflectors A and B are not necessarily oriented on the same plane as any two of ultrasound transducers $X_1$, $X_2$, and $X_3$, accurate three dimensional localization of reflectors A and B requires the utilization of three receivers arranged in a triangular orientation, as described above. It will be understood that although in this embodiment three ultrasound transducers are used, device 4 may function according to the principles of the current invention with a minimum of two ultrasound transducers, and with more than three ultrasound transducers.

Figure 3:
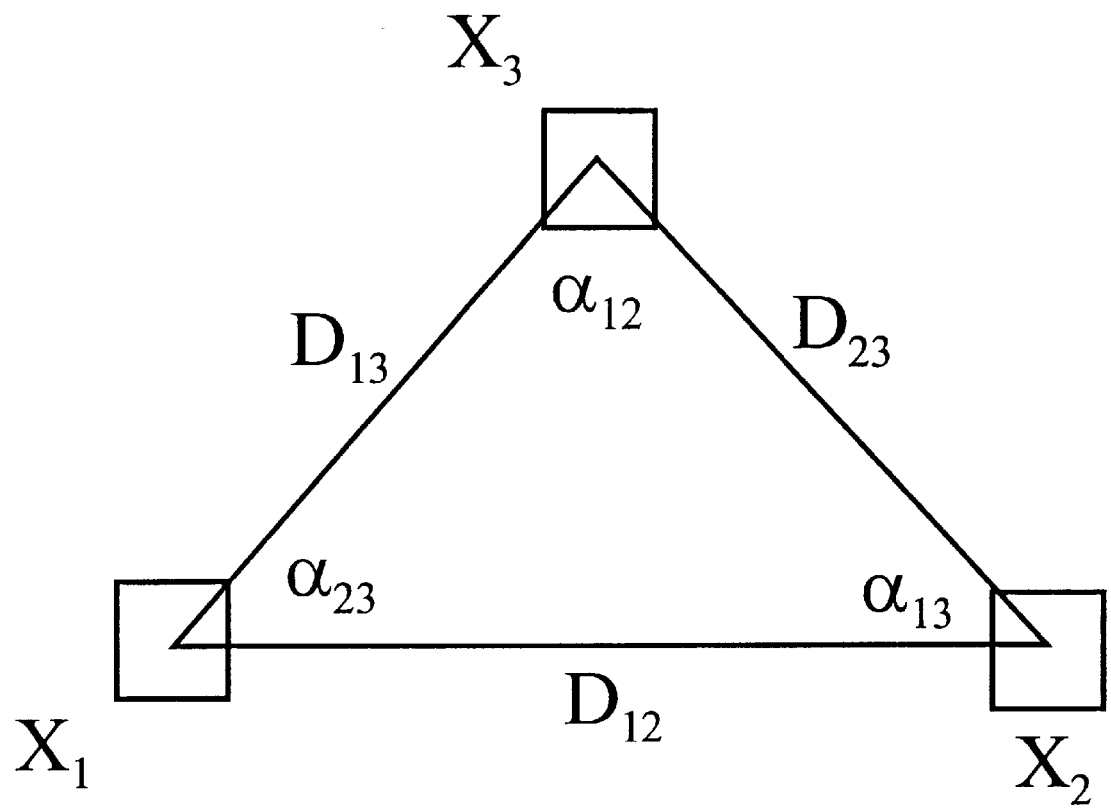
FIG. 3 is a schematic depiction of the geometric relationships between ultrasound transducers according to a first preferred embodiment of the current invention.
Figure 4:
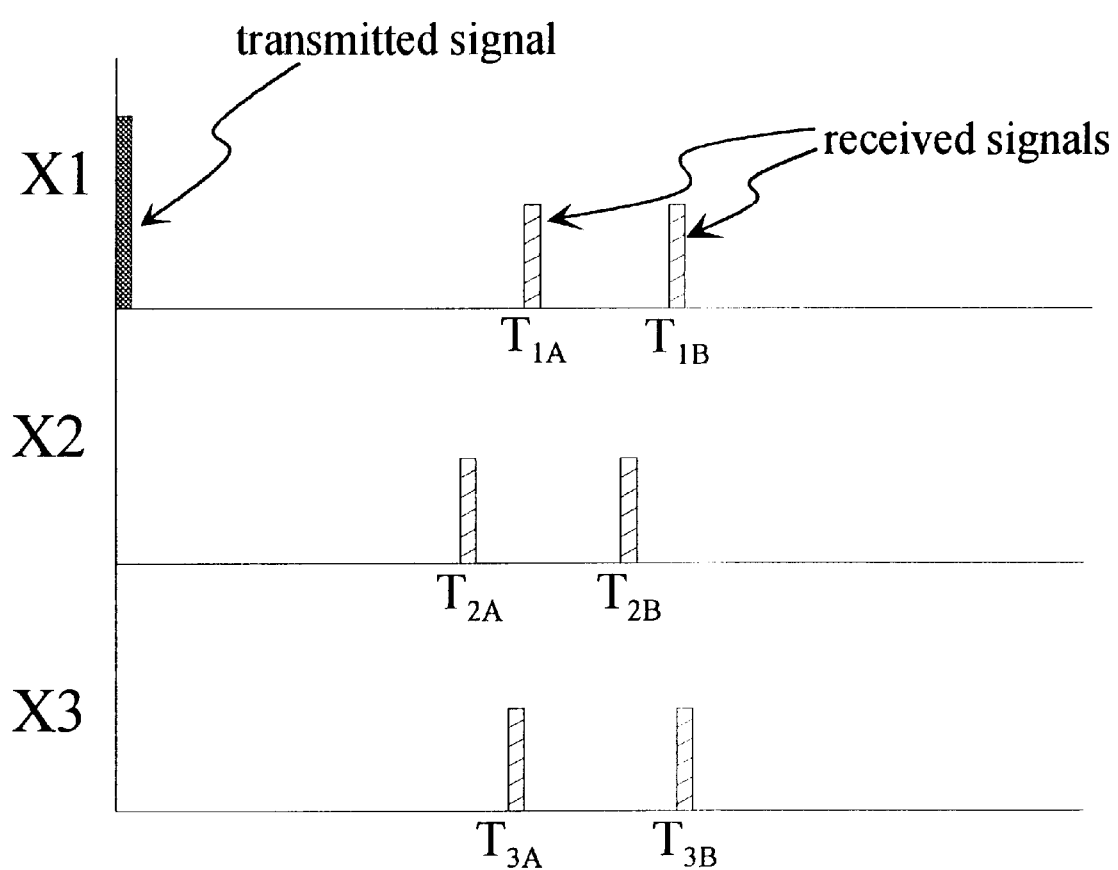
FIG. 4 is a graphic illustration of the timing of transmission and reception of ultrasound signals by ultrasound transducers according to a first preferred embodiment of the current invention.

FIG. 3 schematically depicts the spatial relationships between transducers $X_1$, $X_2$, and $X_3$. In FIGS. 2 and 3, and in the explanatory equations that follow:

$D_{13}$ represents the distance between transducers $X_1$ and $X_3$ $D_{23}$ represents the distance between transducers $X_2$ and $X_3$ $D_{12}$ represents the distance between transducers $X_1$ and $X_2$ $D_{1A}$ represents the distance between transducer $X_1$ and reflector A $D_{1B}$ represents the distance between transducer $X_1$ and reflector B $D_{2A}$ represents the distance between transducer $X_2$ and reflector A $D_{2B}$ represents the distance between transducer $X_2$ and reflector B $D_{3A}$ represents the distance between transducer $X_3$ and reflector A $D_{3B}$ represents the distance between transducer $X_3$ and reflector B FIG. 4 schematically depicts the timing of transmission of an ultrasound signal by transducer $X_1$, and the timing of the reception by transducers $X_1$, $X_2$, and $X_3$ of the echoes reflected off of reflectors A and B. In the figure, and in the explanatory equations that follow:

$T_{1A}$ represents the time at which the ultrasound signal is received at transducer $X_1$ after having been reflected off of reflector A $T_{1B}$ represents the time at which the ultrasound signal is received at transducer $X_1$ after having been reflected off of reflector B $T_{2A}$ represents the time at which the ultrasound signal is received at transducer $X_2$ after having been reflected off of reflector A $T_{2B}$ represents the time at which the ultrasound signal is received at transducer $X_2$ after having been reflected off of reflector B $T_{3A}$ represents the time at which the ultrasound signal is received at transducer $X_3$ after having been reflected off of reflector A $T_{3B}$ represents the time at which the ultrasound signal is received at transducer $X_3$ after having been reflected off of reflector B The distances between reflectors A and B on one hand, and transducers $X_1$, $X_2$, and $X_3$ on the other, can be calculated from the following equations:

$$D_{1A} = 1540 \times T_{1A}$$

$$D_{1B} = 1540 \times T_{1B}$$

$$D_{2A} = 1540 \times T_{2A} - D_{1A}$$

$$D_{2B} = 1540 \times T_{2B} - D_{1B}$$

$$D_{3A} = 1540 \times T_{2A} - D_{1A}$$

$$D_{3B} = 1540 \times T_{3B} - D_{1B}$$

Where 1540 m/sec is the velocity of sound in biological tissue.

Using the calculated distances, and the geometrical and trigonometrical relationships between transducers $X_1$, $X_2$, and $X_3$, the distance between reflectors A and B can be calculated. The calculation of cervical dilation is similar in all embodiments of the current invention, the only differences being in the manner in which $D_{1A}$, $D_{1B}$, $D_{2A}$, $D_{2B}$, $D_{3A}$, and $D_{3B}$ are obtained.

Figure 5:
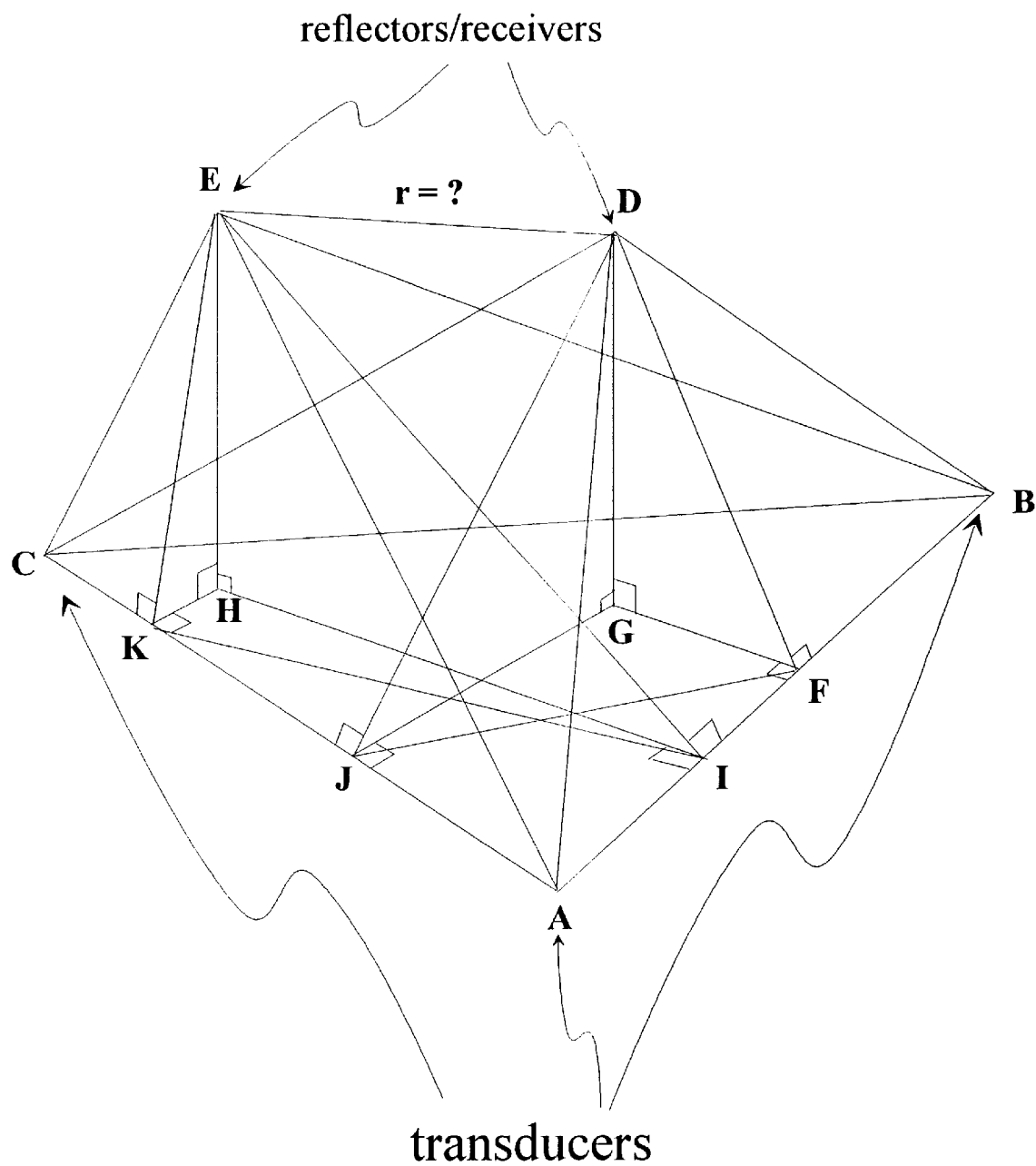
FIG. 5 is an illustration of the geometric relationships underlying the calculation of the distance between two ultrasound reflectors.

FIG. 5 illustrates the geometric relationships underlying the calculation of the distance between two ultrasound reflectors. In this figure, the reflectors are labeled D and E, and the transducers are labeled A, B, and C. The algorithm for performing the calculation, with reference to FIG. 5, is as follows:

$$ED = r = ?$$

$$ED = \sqrt{(AF-AI)^2 + (HI-GF)^2 + (HE-GD)^2}$$

where $$AF = \frac{AD^2 + AB^2 - BD^2}{2 \cdot AB}$$

$$AI = \frac{AE^2 + AB^2 - BE^2}{2 \cdot AB}$$

$$HI = \frac{KI \cdot \sin(90 - \angle AKI)}{\sin(180 - \angle BAC)}$$

$$GF = \frac{JF \cdot \sin(90 - \angle AJF)}{\sin(180 - \angle BAC)}$$

$$HE = \sqrt{[AE \cdot \sin(\angle BAE)]^2 - \left[\frac{KI \cdot \sin(90 - \angle AKI)}{\sin(180 - \angle BAC)}\right]^2}$$

$$GD = \sqrt{[AD \cdot \sin(\angle BAD)]^2 - \left[\frac{JF \cdot \sin(90 - \angle AJF)}{\sin(180 - \angle BAC)}\right]^2}$$

and where $$KI = \sqrt{AI^2 + AK^2 - 2 \cdot AI \cdot AK \cdot \cos(\angle BAC)}$$

$$AK = \frac{AE^2 + AC^2 - CE^2}{2 \cdot AC}$$

$$\angle AKI = \cos^{-1}\left(\frac{AK^2 + KI^2 - AI^2}{2 \cdot AK \cdot KI}\right)$$

$$\angle BAC = \cos^{-1}\left(\frac{AB^2 + AC^2 - BC^2}{2 \cdot AB \cdot AC}\right)$$

$$JF = \sqrt{AF^2 + AJ^2 - 2 \cdot AF \cdot AJ \cdot \cos(\angle BAC)}$$

$$AJ = \frac{AD^2 + AC^2 - CD^2}{2 \cdot AC}$$

$$\angle AJF = \cos^{-1}\left(\frac{AJ^2 + JF^2 - AF^2}{2 \cdot AJ \cdot JF}\right)$$

$$\angle BAE = \cos^{-1}\left(\frac{AB^2 + AE^2 - BE^2}{2 \cdot AB \cdot AE}\right)$$

$$\angle BAD = \cos^{-1}\left(\frac{AB^2 + AD^2 - BD^2}{2 \cdot AB \cdot AD}\right)$$

Figure 6:
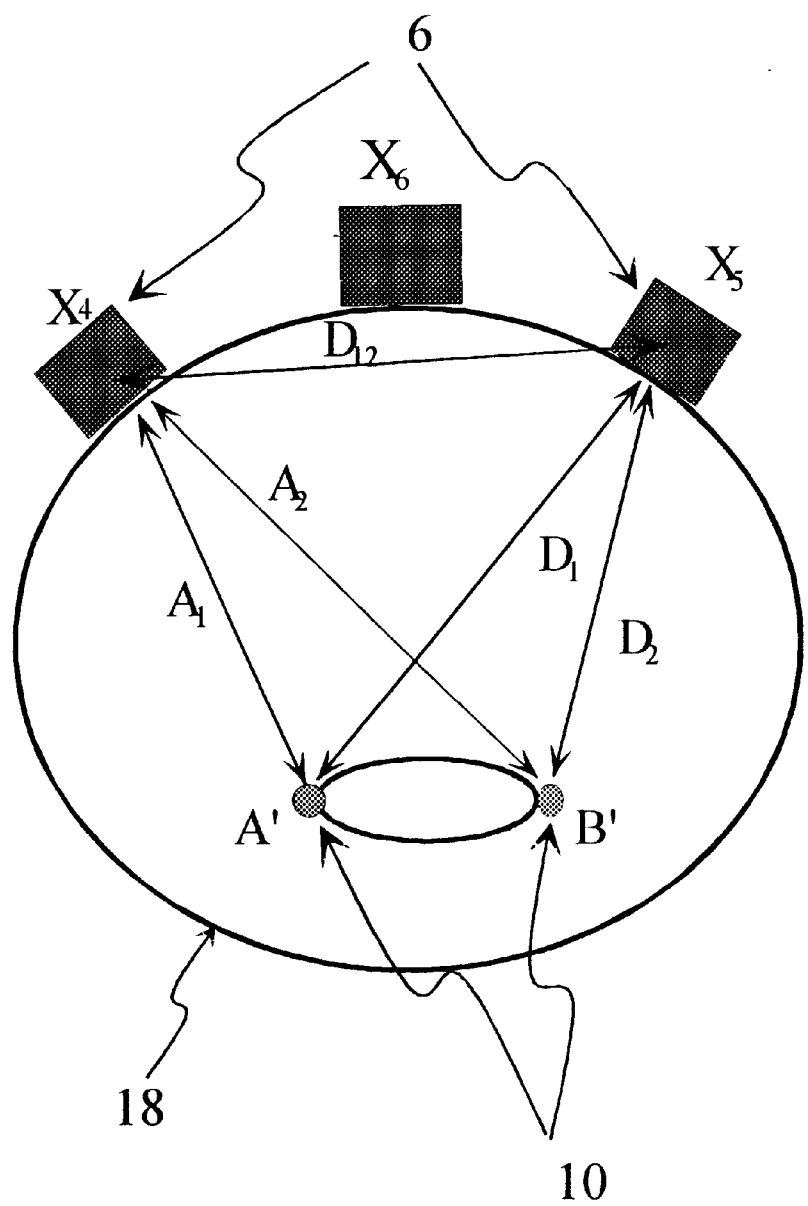
FIG. 6 is a schematic depiction of the distances and spatial relationships between extracorporeal ultrasound transducers and cervical ultrasound reflectors according to a second preferred embodiment of the current invention.

FIG. 6 illustrates the principles underlying a second preferred embodiment of the current invention. In this embodiment, ultrasound transducers 6 comprise three transmitter/receiver pairs $X_4$, $X_5$, and $X_6$, which are positioned on the abdomen of patient 18, and ultrasound reflectors 10 comprise two identical reflectors A' and B', which are attached to essentially opposite sides of the external cervical os, in a manner similar to that described for the first preferred embodiment above. Each one of ultrasound transducers $X_4$, $X_5$, and $X_6$ transmits an acoustic signal in its turn, as determined by DPU 2. For each transmitted signal, all three of ultrasound transducers $X_4$, $X_5$, and $X_6$ receive a reflected signal from reflectors A' and B', and, in addition, the two transducers which did not transmit the signal at that time receive the incident transmitted acoustic signal directly. The time lag from transmission of signal to reception of signal is used by DPU 2 to calculate the distance between each of ultrasound transducers $X_4$, $X_5$, and $X_6$ and each of reflectors A' and B', as described below. In FIG. 5, $A_1$ represents the distance between transducer $X_4$ and reflector A', $A_2$ represents the distance between transducer $X_4$ and reflector B', $D_1$ represents the distance between transducer $X_5$ and reflector A', and $D_2$ represents the distance between transducer $X_5$ and reflector B'.

Figure 7:
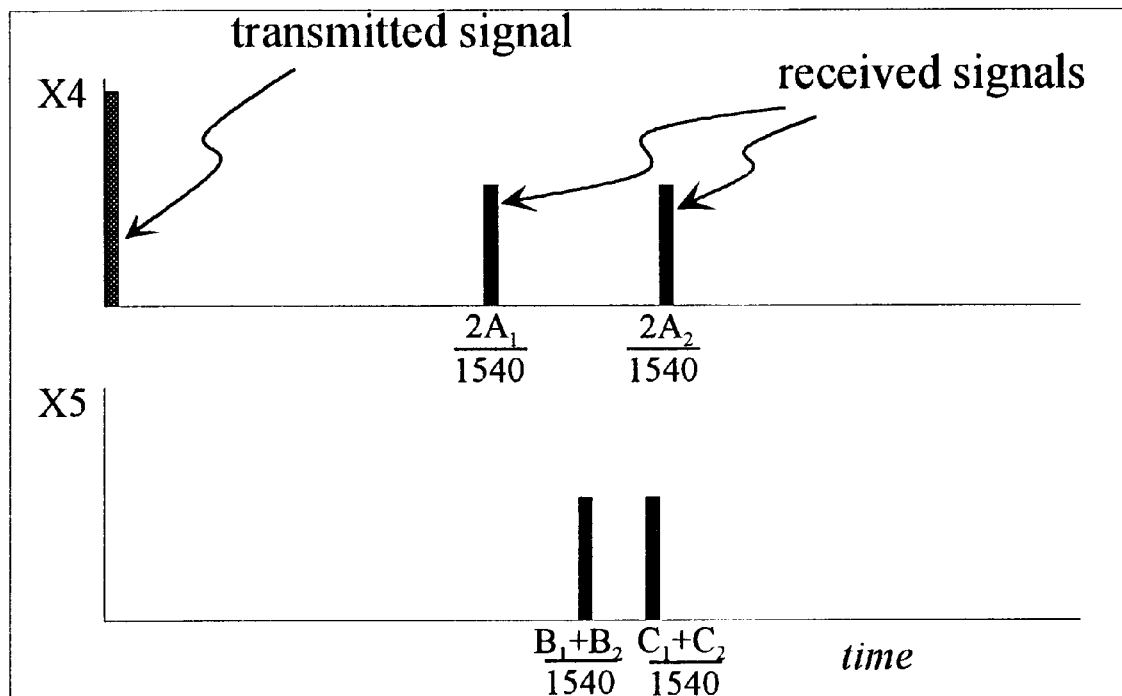
FIG. 7 is a graphic illustration of the timing of transmission and reception of ultrasound signals by ultrasound transducers according to a second preferred embodiment of the current invention.
Figure 7:
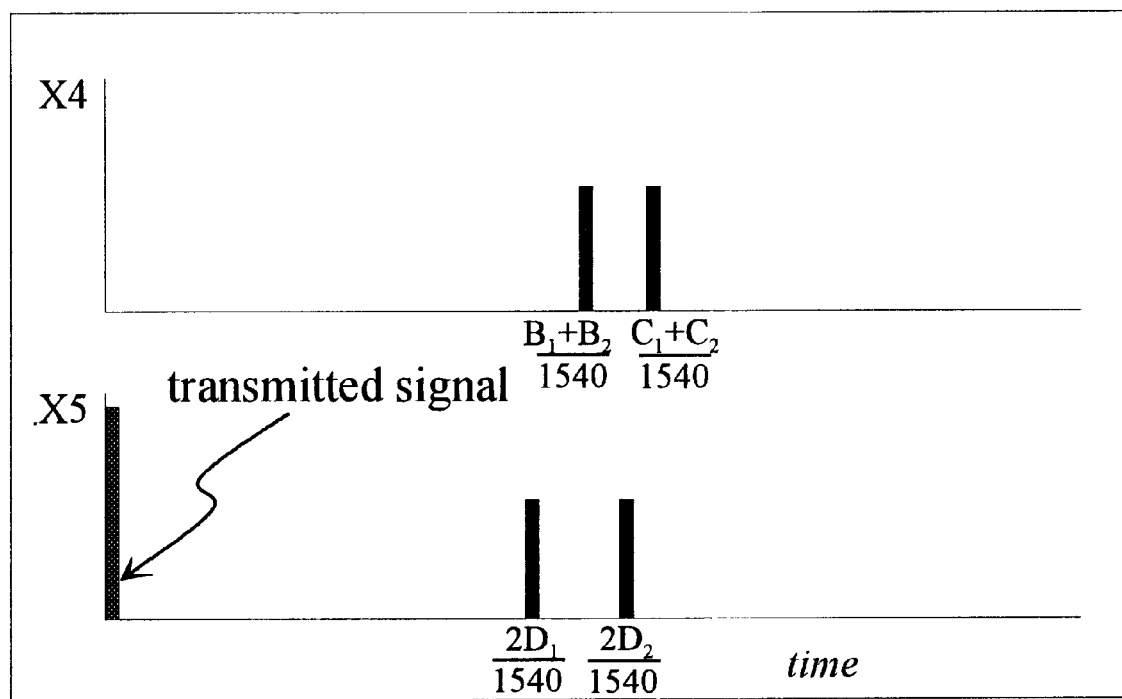

FIG. 7 is a graphic illustration of temporal relationships, in seconds, between signals transmitted and received by transducers $X_4$, and $X_5$, according to the second preferred embodiment of the current invention. In this embodiment, the spectral characteristics of the reflected echoes do not identify the reflector of origin for each echo, but rather, the measured time between signal transmission and reflected echo reception by each transducer is used to identify which echo originated from which reflector. In keeping with the nomenclature of FIG. 5, in FIG. 6 $A_1$ represents the distance between transducer $X_4$ and one of reflectors A' and B', while $A_2$ represents the distance between transducer $X_4$ and the other of reflectors A' and B'. So too, $D_1$ represents the distance between transducer $X_5$ and one of reflectors A' and B', and $D_2$ represents distance between transducer $X_5$ and the other of reflectors A' and B'.

For purposes of illustration, the method of reflector localization utilized in this embodiment will be explained with regard to two transducers ($X_4$ and $X_5$) only, although it will be understood that three transducers are necessary to achieve accurate three-dimensional localization. The upper panel of FIG. 6 shows the timing of signal transmission and reception by transducers $X_4$ and $X_5$ when transducer $X_4$ transmits an ultrasound pulse. The distance that the signal has traveled is divided by the mean velocity of sound in the biological tissue. As can be seen, transducers $X_4$ and $X_5$ each receive two reflected echoes. Similarly, the lower panel of FIG. 6 depicts the timing of signal reception when transducer $X_5$ is the transmitting transducer. Note that the pulses received by the non-transmitting transducer from each reflector are at the same time delay regardless of which transducer is the transmitting transducer, since the distance traversed by an acoustic signal from transmitter to reflector to non-transmitting receiver is the same, regardless of the direction of transmission and reception. With regard to the echoes received by the non-transmitting receiver, the first received echo is labeled $B_1+B_2$ (where $B_1$ is the travel time between the transmitter and an unlocalized reflector, and $B_2$ is the travel time between the unlocalized reflector and the non-transmitting receiver), and the second received echo is labeled $C_1+C_2$ (where $C_1$ is the travel time between the transmitter and an unlocalized reflector, and $C_2$ is the travel time between the unlocalized reflector and the non-transmitting receiver).

If $A_1$ is the travel time from $X_4$ to one of reflectors A' or B', $2A_1$ will be the travel time from $X_4$ to that reflector and back, and $2A_2$ will be the travel time from $X_4$ to the other reflector and back. Similarly, $2D_1$ and $2D_2$ represent the travel times for echoes received by transducer $X_5$.

Thus, when transducer $X_4$ transmits, $A_1$ is the travel time between $X_4$ and one of reflectors A' or B'. $A_1$ is also the first part of the travel time for the same signal on its way to $X_5$. Prior to identifying which echo originates from which reflector, it is not known whether the second part of the travel time for this signal is $D_1$ or $D_2$. Furthermore, the full travel time between transducers $X_4$ and $X_5$ via one of reflectors A' or B' may be equal to either $C_1+C_2$ or $B_1+B_2$.

Thus, if $A_1$ is defined as the travel time to reflector A', analysis of the time delays between signal transmission and signal reception will show only one of the following four equations to be valid:

$$A_1+D_1=B_1+B_2$$

$$A_1+D_2=B_1+B_2$$

$$A_1+D_1=C_1+C_2$$

$$A_1+D_2=C_1+C_2$$

Similarly, with regard to reflector B', only one of the following four equations will be found to be valid:

$$A_2+D_1=B_1+B_2$$

$$A_2+D_2=B_1+B_2$$

$$A_2+D_1=C_1+C_2$$

$$A_2+D_2=C_1+C_2$$

The valid equation identifies which A and D signal pair is a reflection from the same reflector to the two receivers. The resultant data facilitates trigonometric calculation of the relative locations of reflectors A' and B'.

For purposes of illustration, let us assume that the valid equation is $A_1+D_1=B_1+B_2$. This means that there is a reflector at $A_1$ seconds away from $X_4$ and $D_1$ sec away from $X_5$. This also means that the other reflector is $A_2$ seconds away from $X_4$ and $D_2$ sec away from $X_5$. Using this data, a triangle can be constructed for each reflector, such that the base of the triangle is the distance between $X_4$ and $X_5$, and the remaining sides of the triangle are $A_1$ and $D_1$. The height of the triangle, if rotated using the base of the triangle as an axis, describes a circle that includes all possible loci of the reflector in question. A second such circle is then constructed using another pair of transducers (out of the three transducers comprising ultrasound transducers 6) in the same manner. The intersection between these two circles identifies the exact location of the reflector.

In a third preferred embodiment of the current invention, two passive acoustic receivers are placed on the cervical os instead of ultrasound reflectors 10. Passive receivers may be made of piezoelectric material such as PVDF, shaped as simple discs, and are isolated from the conducting environment by a layer of silicone. The time delay or phase difference between signal transmission by each of ultrasound transducers 6 and signal reception by the passive receivers is measured by DPU 2, and localization of the passive receivers calculated by standard trigonometric techniques well known within the art. In this embodiment, the passive receivers are connected to DPU 2 by means of a connective cable passing out of the vagina of patient 18. Although the internally placed components are more complex and expensive, acoustic signal identification and analysis are simpler than that described for the previous embodiments. This also enables the simple addition of a third element —a passive receiver attached to the newborn's presenting part. This addition allows continuous measurement of the advancement of the newborn through the cervix by comparing its location at different times.

In a fourth embodiment of the current invention, ultrasound transducers 6 are replaced by a transducer array and electronic circuits for shaping and directing the transmitted and received acoustic signals, in the form of a beam. In this embodiment, at least two but possibly several reflectors are located on the cervical os. The beam shaping elements of the transducer array are delay lines, each having a different delay. As a result, the transducer array is able to receive acoustic signals originating from a single direction only. As the angle from which the signal is received is controlled and known, localization sensitivity is enhanced. Functioning of the beam shaping elements is controlled by the processor of DPU 2. The transducer array thus performs directional transmission and reception in a manner similar to that of a radar system. The time delay between transmission and reception of the acoustic signals, and the angle from which the returning echoes are received, are analyzed by DPU 2 to calculate the location of the reflector or reflectors being monitored.

There has therefore been described an ultrasound-based cervical dilation monitor which is capable of accurately and automatically monitoring the progress of cervical dilation and decent of the presenting part, without the need to introduce an ultrasound probe into the vagina. The monitor is unique inasmuch as the ultrasound transmitter is located extracorporeally, and ultrasound reflectors or passive ultrasound receivers are located within the birth canal of the mother, marking the position of the fetal presenting part or the diameter of the cervical os.

What is claimed is:

1. A device for monitoring the progress of labor in a subject, comprising
    a) at least one extracorporeal ultrasound transmitter, operative to transmit ultrasound signals into the subject;
    b) at least one inorganic ultrasound reflector, operative to reflect said transmitted ultrasound signals, said at least one reflector being placeable on an internal body surface within the subject;
    c) at least one extracorporeal ultrasound receiver, operative to receive said reflected ultrasound signals, and
    d) a processor, operative to calculate a location of said reflector from said received reflected ultrasound signals, said location being a descriptor of the progress of labor in the subject.

2. The device of claim 1, wherein said at least one extracorporeal ultrasound transmitter is adopted to be placed on the abdomen of the subject.

3. The device of claim 1, wherein said at least one ultrasound transmitter includes a transducer array.

4. The device of claim 1, wherein said at least one reflector includes a material selected from the group consisting of steel and air.

5. The device of claim 1, wherein said at least one reflector is adapted to be placed on an external cervical os.

6. The device of claim 1, wherein said at least one reflector is adapted to be placed on a presenting part of a fetus.

7. The device of claim 1, wherein said extracorporeal ultrasound receiver is adopted to be placed on the abdomen of the subject.

8. The device of claim 1, wherein said processor is adapted to calculate said locations from said received reflected ultrasound signals by measuring an ultrasound signal parameter selected from the group consisting of an ultrasound signal phase shift and an ultrasound signal time of flight.

9. The device of claim 1, wherein said descriptor is selected from the group consisting of a relative location of a fetal presenting part and a diameter of an external cervical os.

10. A method for monitoring the progress of labor in a subject, comprising
    a) transmitting ultrasound signals from an extracorporeal location;
    b) reflecting said transmitted ultrasound signals off at least one inorganic reflector at an internal body surface of the subject;
    c) receiving said reflected signals at an extracorporeal location, and
    d) calculating a descriptor of the progress of labor from said received reflected signals.

11. The method of claim 10, wherein said ultrasound signals are transmitted sequentially from a transducer array.

12. The method of claim 10, wherein said extracorporeal location includes an abdomen of the subject.

13. The method of claim 10, wherein said internal body surface is selected from the group consisting of an external cervical os and a fetal presenting part.

14. The method of claim 10, wherein said calculating includes measuring an ultrasound signal parameter selected from the group consisting of an ultrasound signal phase shift and an ultrasound signal time of flight, and using said measured parameter to describe a trigonometric relationship between said at least one inorganic reflectors.

15. The method of claim 10, wherein said descriptor is selected from the group consisting of a diameter of an external cervical os and a relative location of a fetal presenting part.

* * * * *

UNITED STATES PATENT AND TRADEMARK OFFICE
CERTIFICATE OF CORRECTION

PATENT NO. : 6,270,458 B1
DATED : August 7, 2001
INVENTOR(S) : Ofer Barnea

It is certified that error appears in the above-identified patent and that said Letters Patent is hereby corrected as shown below:

<u>Column 12,</u>
Line 12, the word "adopted" was inserted instead of -- adapted --

Signed and Sealed this

Thirtieth Day of April, 2002

Attest:

Attesting Officer

JAMES E. ROGAN
*Director of the United States Patent and Trademark Office*